United States Patent
Brodbeck

(10) Patent No.: US 6,755,651 B2
(45) Date of Patent: Jun. 29, 2004

(54) DEVICE FOR RECONSTRUCTING TEETH

(76) Inventor: Urs Brodbeck, Lavaterstrasse 53, CH-8002, Zurich (CH)

( * ) Notice: Subject to any disclaimer, the term of this patent is extended or adjusted under 35 U.S.C. 154(b) by 48 days.

(21) Appl. No.: 10/114,272

(22) Filed: Apr. 2, 2002

(65) Prior Publication Data

US 2002/0160334 A1 Oct. 31, 2002

Related U.S. Application Data

(63) Continuation of application No. 09/699,204, filed on Oct. 27, 2000, now abandoned, which is a continuation of application No. PCT/CH99/00168, filed on Apr. 26, 1999.

(30) Foreign Application Priority Data

Apr. 27, 1998 (CH) .............................................. 0946/98

(51) Int. Cl.[7] .................................................. A61C 8/00
(52) U.S. Cl. ....................................................... 433/173
(58) Field of Search ................................ 433/173, 172, 433/174, 175

(56) References Cited

U.S. PATENT DOCUMENTS

| | | |
|---|---|---|
| 3,590,485 A | 7/1971 | Chercheve |
| 4,424,037 A | 1/1984 | Ogino et al. |
| 4,812,120 A | 3/1989 | Flanagan et al. |
| 4,854,872 A | 8/1989 | Detsch |
| 4,872,839 A | 10/1989 | Brajnovic |
| 5,040,983 A | 8/1991 | Binon |
| 5,082,442 A | 1/1992 | Rosen |
| 5,106,300 A | 4/1992 | Voitik |
| 5,135,395 A | 8/1992 | Marlin |
| 5,152,687 A | 10/1992 | Amino |
| 5,205,745 A | 4/1993 | Kamiya et al. |
| 5,316,477 A | 5/1994 | Calderon |
| 5,447,435 A | 9/1995 | Brodbeck |
| 5,636,989 A | 6/1997 | Somborac et al. |
| 5,685,714 A | 11/1997 | Beaty et al. |
| 5,702,695 A | 12/1997 | Clokie |
| 5,931,675 A | 8/1999 | Callan |

FOREIGN PATENT DOCUMENTS

| | | |
|---|---|---|
| DE | 42 30 009 A1 | 4/1993 |
| EP | 0 212 929 A2 | 3/1987 |
| EP | 0 477 644 A1 | 4/1992 |

*Primary Examiner*—Kevin Shaver
*Assistant Examiner*—Melba Bumgarner
(74) *Attorney, Agent, or Firm*—Frishauf, Holz, Goodman & Chick, P.C.

(57) ABSTRACT

In a dental implant device for reconstructing teeth, a supporting element and an abutment portion form a single substructure (10). This substructure comprises an inner metal core (13) and an outer sheath (14) that is formed of a ceramic and/or of a composite material. The lower part of the substructure forms the supporting element (12), and the upper abutment portion functions as a retaining mold portion (11) for receiving the tooth crown (3) reconstructed tooth. The retaining mold portion (11) merges at a concavely rounded transition with the supporting element; and the terminal collar of the tooth crown of the reconstructed tooth has a matching convexly rounded run-out, so that in the assembled state, the transition and the run-out form a perfectly congruent seat (15). The outer sheath and the tooth crown have the same color structure and may be made of the same or similar materials.

7 Claims, 5 Drawing Sheets

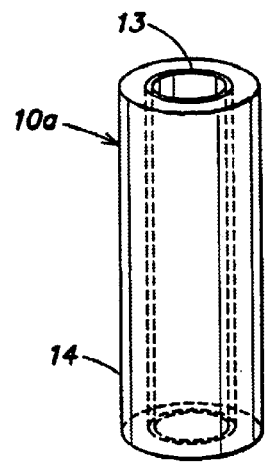
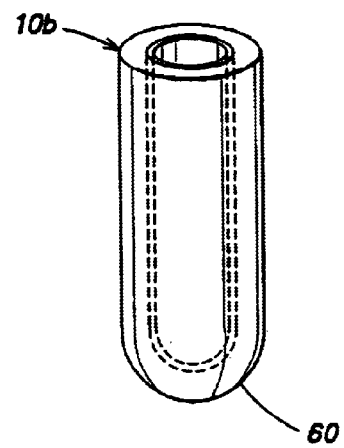
FIG. 5(a)  FIG. 5(b)
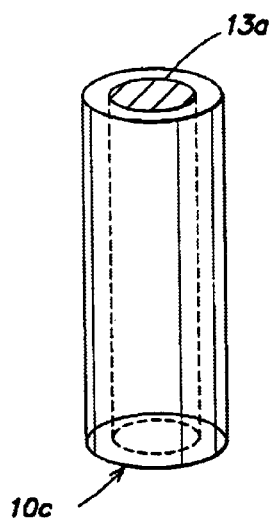
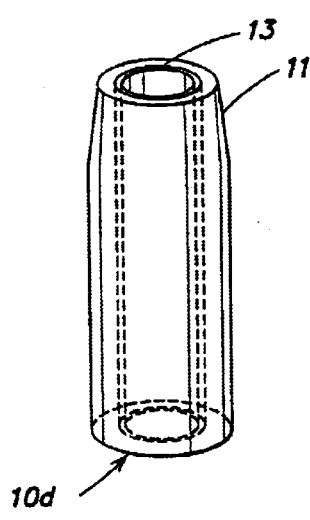
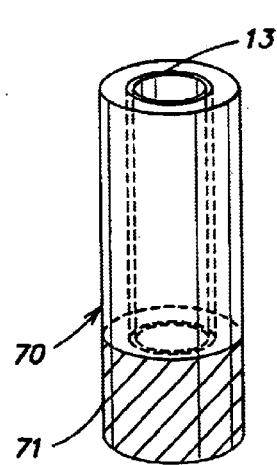
FIG. 5(c)  FIG. 5(d)  FIG. 5(e)

2

DEVICE FOR RECONSTRUCTING TEETH

CROSS-REFERENCE TO RELATED APPLICATION

This application is a continuation of application Ser. No. 09/699,204, filed Oct. 27, 2000, which is a Continuation of International Application No. PCT/CH99/00168 filed Apr. 26, 1999, the entire contents of which are incorporated herein by reference.

FIELD OF THE INVENTION

The present invention relates to a dental implant device for reconstructing teeth.

PRIOR ART

In tooth reconstruction, the implantation technique is becoming more and more important. In assessing the proposals that have been disclosed, one finds that the technical orientation over the years has not substantially changed. In a chronological outline the relevant printed references, one finds that the known implants are always based on a supporting device designed in various different ways, which is incorporated into the jawbone in various ways and which substantially comprises an abutment portion fixed in various ways to the supporting device. The external shape of the abutment portion then forms the seat or support for the reconstructed tooth. These implant parts, which in the prior art are made of titanium or a titanium alloy, have many different shapes, and many different types of connections have been proposed between the supporting device and the abutment portion. The following significant references in the prior art are an indication of the manifold nature of the proposals that have been disclosed. Among many others, the following can be named:

U.S. Pat. Nos. 4,854,872; 4,872,839; 5,082,442; 5,152,687; and European Patent Disclosure No. EP-A1-0 477 644.

In none of the proposals listed above can fundamental problems of the implantation technique be solved. The tooth configuration of every person differs in shape, geometric extent, and position in the dental arch, which is why, in the implants that have been disclosed, a difficult adaptation must always be made in the region of the receiving seat of the abutment portion in the gums if the individual reconstructed tooth deviates from the plane defined by the supporting device and the abutment portion, or, if the dimensions of the root, which are predetermined by the supporting device, should change. It is found that the available commercial selection leaves little room for maneuvering in terms of making the desired adaptations at little effort or expense. For instance, this difficult adaptation may comprise machining the portion of the abutment toward the gum, which abutment acts as a receiving seat for the tooth to be reconstructed, in such a way that a suitable correction in terms of position and shape thereof results. It is evident that performing such machining in the installed state makes major demands on the practitioner both visually and in terms of manual skill. Even a small deviation in machining has an immediate adverse effect on the end product. Corrections to that end are always complicated and not infrequently proved to be merely patch work.

The same is true for the proposals according to U.S. Pat. Nos. 5,040,983; 5,106,300; and 5,135,395, which are distinguished by an especially complex structure between the supporting device and the abutment portion.

Essentially two fundamental problems fail to be solved satisfactorily by any of the above-listed proposals. First, it is demonstrated that if there is even the slightest retraction of the gum, the abutment area becomes visible. This is always apparent from a dark linear curve above the border of the gum (i.e., above the gum line), which always means a perceptible impairment of the aesthetic appearance, leaving something to be desired in terms of acceptance of the disclosed concepts. In seeking a reliable remedy for this, the transition between the supporting device and the abutment portion would have to be shifted to an area deep in the gum, but this is only possible if enough gum is still present. Second, the gap that unavoidably forms at the transition between the supporting device and the abutment portion and at the transition between the abutment portion and the implant proves to be extremely vulnerable to bacterial colonization, which increases the risk of extremely rapid dramatic gum loss and thus completely reverses the success of the reconstruction.

Conversely, in German Patent Disclosure DE-A1-42 30 009, a proposal has been disclosed that is capable of remedying substantial disadvantages of the prior art disclosed prior to it. The disclosed technique can be seen as an improvement since every reconstruction is based on an individual or standardized abutment, which can then be prepared to make an individualized retaining mold for the reconstructed tooth. The abutment itself comprises a metal core, with a sheath made of ceramic, a plastic, or composite material. The preferably plastic sheath extends deep into the anchoring region of the abutment, in such a way that even if there is a drastic gum loss, the metal terminal core of the abutment, or the supporting device, should not become visible, thus surely considerably enhancing the acceptance of this proposal compared to the prior art disclosed prior to it. However, an aspect of this proposal that can be emphasized as still unsatisfactory is the transition, located deep in the gum, between the metal supporting device and the abutment. This transition, however perfectly achieved, always forms a gap bacteriologically, and as a result, there is an intrinsic vulnerability to bacterial colonization. A gap shifted as deep as possible into the gum for aesthetic reasons can be reached by conventional cleaning means only with great difficulty. The resultant bacteriological problems are notorious in dentistry.

SUMMARY OF THE INVENTION

The object of the present invention is to provide an improved dental implant technique in which all of the disadvantages, with individual or multiple effect, of the implants of the prior art are overcome.

Fundamentally, the present invention proposes integrating or fusing the supporting element and abutment portion into a single unit. This single unit performs the function of a substructure. The lower region of the substructure serves as a supporting element, and the upper region of the substructure takes on all the functions of a technologically highly placed abutment portion.

According to the present invention a dental implant device for reconstructing teeth comprises a supporting element adapted to be solidly connected in a jawbone and ending in a gingival region; and an abutment portion extending from the supporting element and extending above the gingival region, which abutment portion serves as a receiving seat for a tooth crown of a tooth to be reconstructed. The supporting element and the abutment portion form a single unitary substructure or a multipart substructure. The single unitary substructure comprises an inner metal core and an outer sheath surrounding the inner metal core, the outer sheath being made of a ceramic and/or a composite material having substantially the same color as the tooth crown of the tooth to be reconstructed.

Exemplary embodiments of the invention will be described in detail below. Any elements not necessary for immediate comprehension of the invention have been left out. In the various drawing figures, identical elements are identified by the same reference numerals.

BRIEF DESCRIPTION OF THE DRAWINGS

FIGS. 5(a)–5(e) show various initial forms of the substructure of dental implant devices according to the present invention;

DETAILED DESCRIPTION

Figure 1:
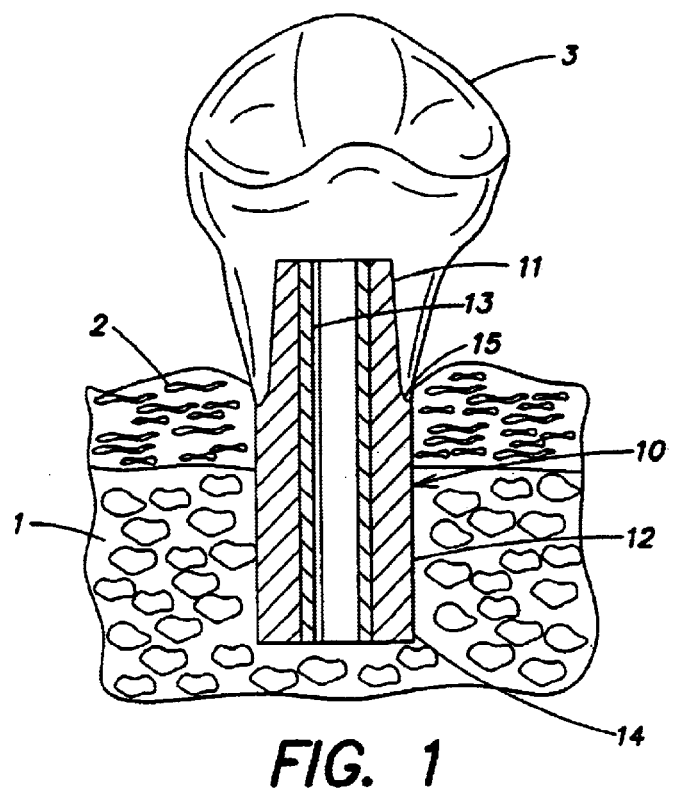
FIG. 1 shows a partial cross-sectional view of a dental implant device for reconstructing teeth, in which the lower part is anchored in the jawbone by a press fit.

FIG. 1 shows a substructure 10 of a dental implant device of the present invention, comprising a single piece, which performs the function of both a supporting element and an abutment portion. This substructure 10 is intrinsically a single unit and comprises a metal, tubular base body or core 13, preferably made of titanium or a titanium alloy, and an outer sheath 14. The outer sheath 14 comprises a ceramic and/or composite material which has substantially the same color as the tooth crown 3. A lower part of the substructure 10 forms the supporting element 12 of the dental implant and is anchored in the jawbone 1 by a press fit. An upper part 11 of the substructure 10 forms the receiving seat of a tooth to be reconstructed 3. The seat 11 is shown as a retaining tapered portion (retaining mold or abutment 11). The gingiva (gum) 2 is prepared surgically at the implant site to such an extent that the supporting element 12 of the substructure 10 can be anchored in the jawbone. Precise positioning of the supporting element 12 is a prerequisite for the success of the entire reconstruction. After the healing phase, essentially only the retaining mold portion 11 protrudes from the gingiva 2. The transition portion 15 between the supporting element 12 and the retaining mold portion 11 is concealed by the healed gingiva 2.

The transition portion 15 between the retaining mold (abutment) portion 11 and the supporting element 12 is formed by a concavely rounded run-out, and the terminal (lower portion) collar of the tooth crown 3 is characterized by a matching convexly rounded termination. The concave run-out of the retaining mold portion 11 and the convex termination of the terminal collar of the tooth crown 3 form a seat relative to one another at the transition 15, which forms a perfect, congruent geometrical shape of the two parts that can be joined together. This seat at 15 is furthermore distinguished by the fact that it is embodied as maximally gap- and offset-free, which not only improves the visual appearance, but also eliminates the formation of a gap which would be threatened bacteriologically by the criteria of dentistry (see the description of FIG. 4 hereinbelow). The tooth crown 3 and the outer sheath 12 have substantially the same color.

The aforementioned retaining mold portion 11 can be preformed or can be easily prepared individually, either before or after installation in the bone, and either by corrective machining (i.e., with a dental drill or the like) of the outer surface thereof or by mounting a thin aligning centering sleeve, not shown in detail, which then forms the new retaining mold. To a certain extent, the retaining mold portion 11 can be provided skewed or slanted relative to the original plane (see FIGS. 6(a) and 6(b)) or can be machined in that way, so that in each case optimization in terms of shape and position can be achieved in the tooth reconstruction, which is indicated especially whenever the reconstruction is to be made between two healthy teeth. Once the reconstructed tooth 3 is inserted and anchored on the retaining mold portion 11, the reconstruction is concluded. If the retaining mold portion 11 has no self-impeding or self-locking structure, the fixation between the outer surface of the retaining mold portion 11 and the inner surface of the hollow inner portion of the reconstruction tooth crown 3 can be accomplished by an adhesive.

Figure 7:
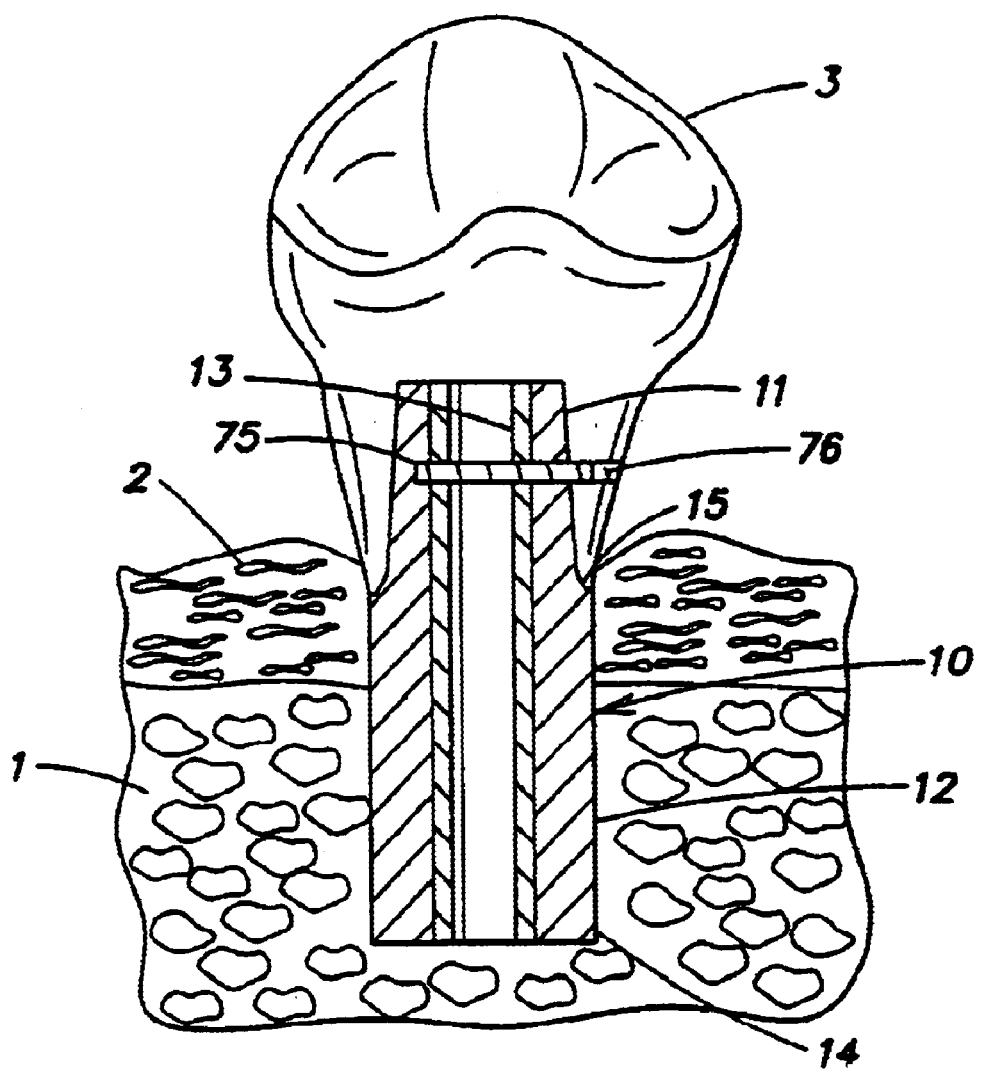
FIG. 7 shows a partial cross-sectional view of a modified embodiment.

As shown in FIG. 7, the fixation of the reconstruction tooth crown 3 to the substructure 10 beneath can be attained by means of a separable connection, such as a screw or pin 75, which can be mounted above the gingiva 2 and radially anchored to the metal core 13. A screw 75 introduced for instance from the outside, radially through the lower portion of the reconstruction tooth crown 3, can then easily be concealed by a closing insert 76 of the same material as the reconstruction tooth crown 3 itself or by a dental "filling" material having the same color as the tooth crown 3. This variant of fastening is illustrated by way of example in FIG. 7, but is readily known to one skilled in the art.

Even if a drastic worsening of the health of the gingiva 2 leads to gum loss, the reconstruction described above causes no impairment in the outer aesthetic appearance of the tooth, and accordingly there is no need to fear gingival clearance, because the sheath 14 of the substructure device 10 has the same color structure throughout as the tooth crown 3. This is especially important whenever the gum loss has progressed to below the end of the collar of the reconstructed tooth 3 in the region of the seat 15. As shown in FIG. 1, the lower collar of the reconstructed tooth 3 is embodied as gap- and offset-free by virtue of the seat-forming transition 15 between the retaining mold portion 11 and the supporting element 12. A parting line, although always present, is not visually apparent, since both reconstruction elements have the same color structure. In any case, with the structure (the tooth, crown portion 3 and the outer sheath 14) according to the present invention, in the event of a drastic gum loss, a remedy is provided at any time in the simplest possible way, because without destroying the substructure 10, a new adapted tooth crown 3 can be attached, making this reconstruction highly amenable to retrofitting.

Figure 2:
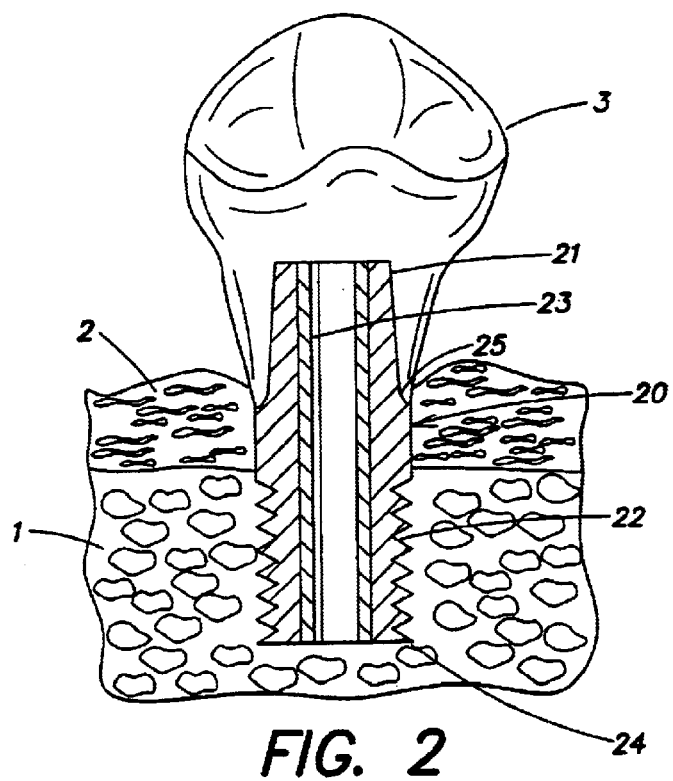
FIG. 2 shows a partial cross-sectional view of a dental implant device for reconstructing teeth, in which the lower part is anchored in the jawbone by a threaded connection with the jawbone.

FIG. 2 differs from FIG. 1 only in that the supporting element 22 of the substructure 20 is provided with a thread, which is screwed into the jawbone 1. Otherwise, the embodiment of FIG. 2 is the same as the embodiment of FIG. 1.

Figure 3:
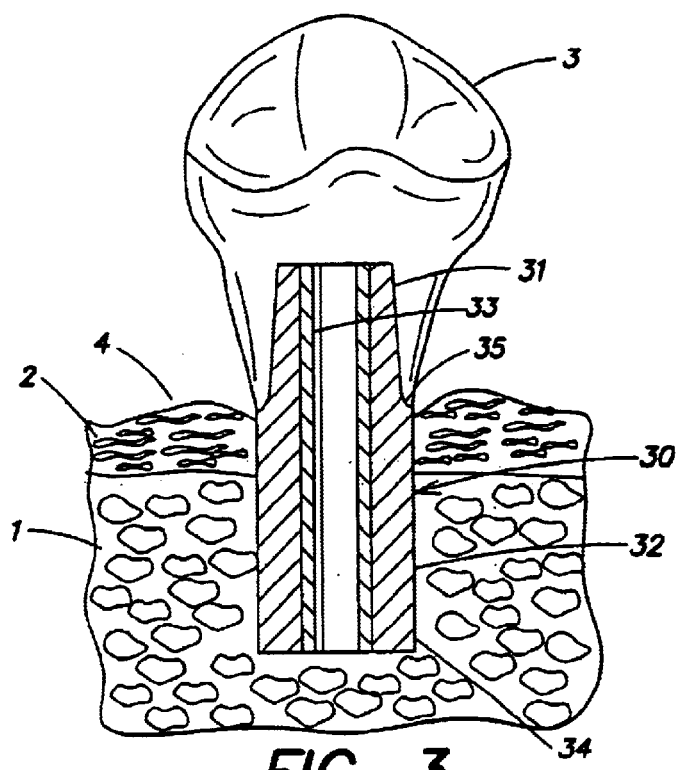
FIG. 3 shows a partial cross-sectional view of a dental implant device for reconstructing teeth, in which the terminal collar of the reconstructed tooth ends above the gingival margin.

In FIG. 3, the construction of the substructure 30 and of the reconstructed tooth 3, corresponds to the structure of FIG. 2. One difference here is that the seat 35, which corresponds to the seat 15 of FIG. 1, is kept above the gingival margin 4. As described above with reference to FIG. 1, there is no need to fear any destruction or impairment of the aesthetic appearance since the outer sheath 34 and the tooth crown 3 are of the same color and the parting line therebetween is not readily visible. Other remarks on this situation can be found in the description of FIG. 4.

Figure 4:
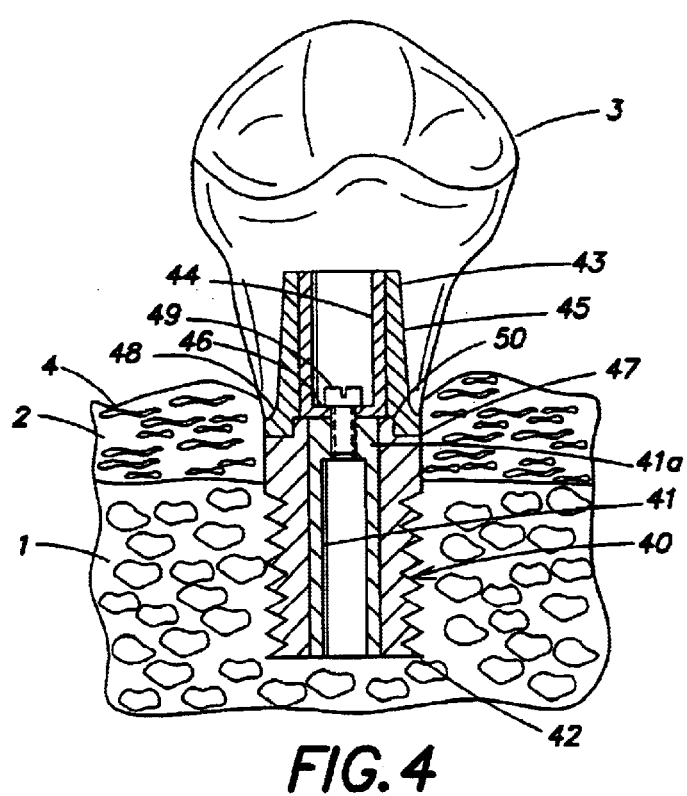
FIG. 4 shows a partial cross-sectional view of a two-piece dental implant device for reconstructing teeth showing the supporting device and the abutment portion assembled together.

FIG. 4 shows a reconstruction in which the original single unit substructure of any of FIGS. 1–3 is split apart into multiple pieces for implantation reasons. The advantages explained in conjunction with the other drawing figures are attained as well by the structure of FIG. 4, and other advantages are attained by means of the special mounting configuration of FIG. 4. The difference from the embodiments shown in the preceding figures is that the supporting element 40 and the abutment portion 43 here are produced individually but are integratively assembled together. This is done in such a way that the visual perception implies no loss of the aesthetic appearance. The supporting element 40 and abutment portion 43 each comprise a respective metal tubular core 41, 44 and outer sheath 42, 45, preferably comprising ceramic and/or a composite material. In the upper region of the supporting element 40, the metal tubular core 41 of the supporting element 40 has a thickened portion 41a on the inside. By comparison, at the lower part of the abutment portion 43, toward the supporting element 40, the metal tubular core 44 of the abutment portion 43 has a shoulder 46 with an opening. Through this opening, a screw 49 threadably engages with the thickened portion 41a of the supporting element 40 in such a way that by means of the screw 49, both the supporting element 40 and the abutment portion 43 are firmly screwed together. The integrative assembly of the two parts 40, 43 causes the ceramic sheath portions thereof (which are of the same color) to press against one another at a parting line 47. The centering of the two parts 40, 43 of the substructure is performed by an annular protrusion 50, which projects from the ceramic sheath 42 of the supporting element 40 and into the opposed ceramic sheath 45 of the abutment portion 43. Although with this configuration it is unavoidable that a parting line 47 is created, this is no problem whatever in terms of the aesthetic appearance, because the two sheaths 42, 45 comprise the same material, and the color structure of this same material completely matches that of the tooth crown 3. Moreover, the parting line 47 between the two parts is subject to a strong connection force from the screw 49. Although the term "parting line" 47 is used here, it must be stressed here that purely by the criteria of dentistry, the term "gap" is used if it is even a maximum of 100μ wide. Because of its skillfully conceived integrative joining together, the configuration according to FIG. 4 readily makes it possible for this gap to amount to only a small fraction of 100μ (substantially less than 100μ, which means that there is essentially no gap at all. The same is true for the seats 15, 25, 35 and 48, all of which mate so perfectly that any gap formed thereby is only a small fraction of 100μ wide. Therefore, both the parting line 47 and the seat 48, which is embodied similarly to the seats 15, 25, 35 of the preceding FIGS. 1, 2, 3, respectively can likewise be positioned below the gingival surface or margin 4. On the other hand, the situation is such that the seat 48 here can also be placed above the gingival margin 4, such as shown in FIG. 3, without having to fear any impairment of the aesthetic appearance (since the outer elements are of the same color).

FIG. 1 shows a substructure 10 which was preliminarily prepared in the state ready for installation. FIGS. 2–4 show other substructures 20, 30 and 40, respectively.

The substructure 10a of FIG. 5(a) has a cylindrical sheath 14, with a tubular metal inner cylinder 13. This shape is well suited to cases in which the retaining mold portion 11 is to be formed afterward, for example by machining by, for example, the practitioner.

The substructure 10b of FIG. 5(b) is constructed similarly to the substructure 10a of FIG. 5(a), but on the bottom 60 it is closed off with a rounded shape. The substructure 10b of FIG. 5(b) is well suited to cases in which the installation in the jawbone is contemplated by means of a press fit, as in FIG. 1. The rounded bottom 60 can improve ease of installation.

FIG. 5(c) shows another cylindrical substructure 10c, but having a solid metal core 13a. This substructure is used in the same manner as that of FIG. 1. The retaining mold portion 11 thereof can be pre-formed, or machined after or before installation in the gum.

In FIG. 5(d), the substructure 10d is similar to that of FIG. 5(a), but the retaining mold portion 11 is already predetermined (i.e., is pre-formed).

In FIG. 5(e), a multi-part assembled substructure 70 is shown. In the substructure 70, one part 71 of the portion anchored in the jawbone is made of metal and can alternatively be provided with a thread (as shown in FIGS. 2–4). At the top, the retaining mold portion 11 can be machined after or before installation in the gum.

The substructures with smooth outer surfaces are well suited to functioning with a press fit in the jawbone. They can readily be provided with a thread in the lower part, such as shown in FIGS. 2–4, for screwing into the jawbone.

Figure 6A:
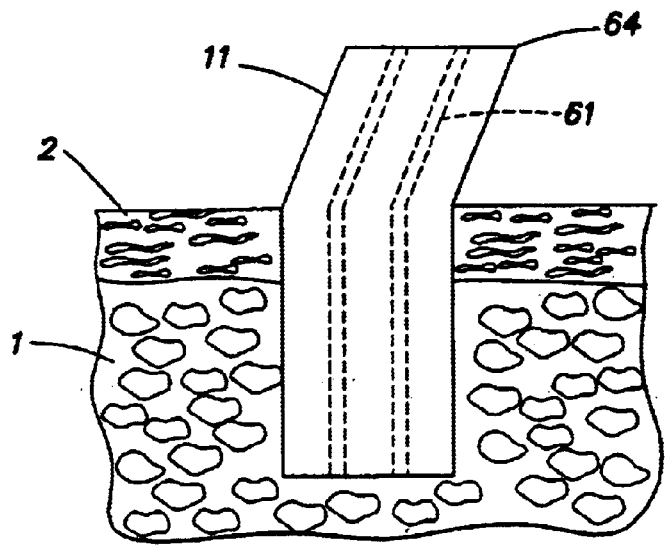
FIGS. 6(a) and 6(b) show substructures of dental implant devices of the present invention with bent upper parts.
Figure 6B:
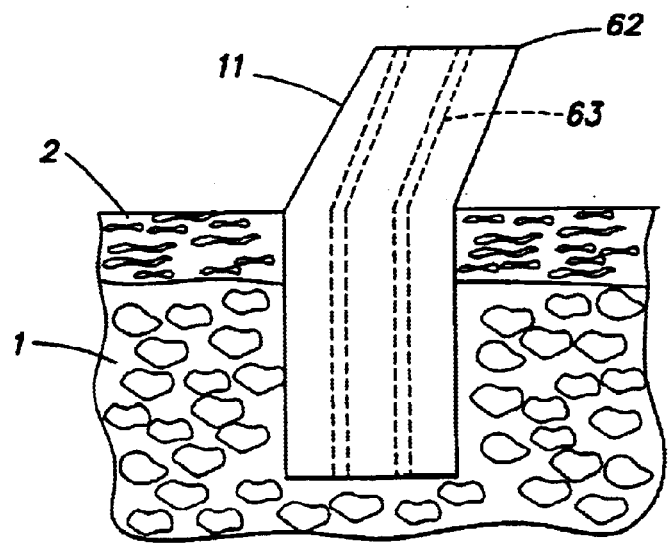

FIGS. 6(a) and 6(b) show two further special substructures wherein the retaining mold portions (upper portions) thereof are bent relative to a plane or axis of the supporting element (lower portion) thereof.

The substructure of FIG. 6(a) has an upper bent portion, in which the metal core 61 extends substantially parallel to the outer sheath 64.

In the substructure of FIG. 6(b), the outer sheath 62 and the metal core 63 of the substructure extend generally trapezoidally relative to one another.

The bent substructures of FIGS. 6(a) and 6(b) will be used wherever it is critical to achieve a skewed or slanted reconstruction.

In summary, the substructure according to the present invention in its entirety comprises an upper part serving as the retaining mold portion and a lower part that performs the function of a supporting element. The transition between the retaining mold portion and the supporting element is formed by a concavely rounded run-out, and the terminal collar of the tooth crown has a matching convexly rounded termination.

The run-out at the transition 15, 25, 35 and 48, and the termination at the terminal collar of the tooth crown, in the installed state, form a congruent, perfect seat relative to one another. This seat is distinguished by being maximally free of gaps and offsets, which improves not only the visual appearance but also prevents the formation of a gap that by the criteria of dentistry is at risk bacteriologically.

The dental implant substructure according to the present invention for reconstructing teeth comprises, over its full length, a metal core and an outer sheath of ceramic and/or composite material. The metal core serves as a supporting material for the outer sheath. Thus, the wall thickness of this outer sheath can be reduced to a minimum (about 0.1 mm) since the outer sheath is supported and strengthened by the inner metal core. The inner metal core can also provide anchoring as needed, where there is a radially made mechanical connection between a reconstructed tooth and the effective retaining mold below it (see FIG. 7).

In a primary embodiment of the present invention, the lower supporting element region of the device is prepared in such a way that it can be anchored in the jawbone, either by a press fit (FIG. 1) or by being screwed in (FIGS. 2–4). Which of these two types of anchoring will be employed depends on the specific case. Whichever form of anchoring comes to be used serves the purpose only of primary stability, which is necessary for optimal grading. The upper region can be embodied in manifold ways as a receiving mold portion for receiving the reconstructed tooth. The retaining mold area is preferably employed for shaping purposes. The shaping of the receiving or retaining mold portion 11 can be done in advance, or it can be shaped by machining after installation.

The essential advantage of the device of the present invention is that a connection that forms a gap between the supporting element and the abutment portion is now no longer present.

The terminal running-out collar of the reconstructed tooth (in the area of the transition portions 15, 25, 35 and 48) preferably ends below the gingival margin. This can be accomplished without risk, since the substructure of the invention, comprised a unit, now no longer has any gap which would cause a bacteriological risk. Since, externally, the entire visible portion of the substructures comprises a ceramic or composite having the same color structure as the reconstruction tooth crown 3 mounted on it, the terminal collar of the reconstructed tooth can readily be positioned even above the gingival margin (as shown in FIG. 3), since for the above reasons the transition (parting line) is not visually apparent. The tooth crown 3 and the outer sheath portions can be made of the same or similar ceramic and/or composite materials. Preferred composite materials are a polymer and a ceramic, and a polymer and a metal.

Although the portion anchored in the jawbone externally comprises an outer sheath of ceramic and/or a composite material, still because of its inner metal core it has adequately great stability and strength so that in this respect there is no risk of breakage of the ceramic body, even though the outer sheath according to the invention can be minimized down to a minimum wall thickness of only about 0.1 mm. A preferred maximum wall thickness of the outer sheath (in all of the embodiments) is about 6 mm. The resistance to breakage of this outer sheath, in cooperation with the inner metal core or base body, is attained both when the substructure itself is installed and later during the intended use of the reconstruction (tooth crown) operatively connected to the supporting element. A risk of breakage was always latent in prior art supporting devices made of a solid ceramic material, and therefore they could not become established in practice, which is why for a long time such insert parts have been rejected for safety reasons. The inner metal core of the present invention overcomes this problem in the prior art.

The substructure according to the present invention can also be made in two parts (see FIG. 4) for implantation reasons. In this arrangement, the parting line formed when the supporting element and abutment portion are put together, is in the region of the ceramic outer sheaths of the two parts, so that because of the construction according to the invention (same color materials and any "gap" is only as small fraction of $100\mu$, there is neither any aesthetic impairment nor any bacteriological risk.

Various modifications and/or alterations of the invention as described hereinabove can be made within the scope of the appended claims. Also, various features of any embodiment can be combined with features of other embodiments consistent therewith, within the scope of the appended claims.

I claim:

1. A dental implant apparatus for reconstructing teeth, the implant apparatus comprising:
    a single unitary substructure (10, 20, 30) having a lower part that can be anchored in a jawbone, and an upper part serving as a receiving element in the gingival region for receiving a reconstructed tooth (3); and
    wherein the lower part of the single unitary substructure (10, 20, 30) that can be anchored in the jawbone comprises a metal member, and the upper part of the single unitary substructure comprises a metal core with an outer sheath (14, 24, 34) made of a ceramic and/or a composite material;
    wherein the receiving element of the single unitary substructure (10, 20, 30) is embodied as a retaining mold portion (11, 21, 31) for receiving the reconstructed tooth (3) and wherein the retaining mold portion has a concavely rounded run-out which is congruent with a lower conclusion of the reconstructed, wherein when the reconstructed tooth is assembled on the retaining mold portion, the retaining mold portion forms a congruent seat (15, 25, 35) with respect to the reconstructed tooth.

2. The apparatus of claim 1, wherein the congruent seat (15, 25, 35) is below a gingival margin (4).

3. The apparatus of claim 1, wherein the congruent seat (15, 25, 35) forms a curved termination.

4. The apparatus of claim 1, wherein the lower part, which can be anchored in the jawbone, of the single unitary substructure is provided with a thread (22, 32).

5. The apparatus of claim 1, wherein the lower part, which can be anchored in the jawbone, of the single unitary substructure is arranged to be anchored in the jawbone by a press fit.

6. The apparatus of claim 1, wherein at least the inner metal core of the upper part of the single unitary substructure comprises a tubular member.

7. The apparatus of claim 1, wherein at least the inner metal core of the upper part of the single unitary substructure comprises a solid body.

* * * * *